(12) United States Patent
Kasai et al.

(10) Patent No.: US 10,151,918 B2
(45) Date of Patent: Dec. 11, 2018

(54) SCANNER, SCANNING ILLUMINATOR, AND SCANNING OBSERVATION APPARATUS

(71) Applicant: OLYMPUS CORPORATION, Tokyo (JP)

(72) Inventors: Yasuaki Kasai, Saitama (JP); Hiroshi Tsuruta, Kanagawa (JP)

(73) Assignee: OLYMPUS CORPORATION, Tokyo (JP)

( * ) Notice: Subject to any disclaimer, the term of this patent is extended or adjusted under 35 U.S.C. 154(b) by 165 days.

(21) Appl. No.: 15/130,141

(22) Filed: Apr. 15, 2016

(65) Prior Publication Data

US 2016/0231561 A1    Aug. 11, 2016

Related U.S. Application Data

(63) Continuation of application No. PCT/JP2014/075733, filed on Sep. 26, 2014.

(30) Foreign Application Priority Data

Oct. 21, 2013  (JP) .................... 2013-218227

(51) Int. Cl.
*G02B 26/10* (2006.01)
*G02B 23/26* (2006.01)
(Continued)

(52) U.S. Cl.
CPC ........ *G02B 26/103* (2013.01); *A61B 1/00006* (2013.01); *A61B 1/00172* (2013.01);
(Continued)

(58) Field of Classification Search
CPC .. G02B 26/103; G02B 23/2484; G02B 23/26; A61B 1/07; A61B 1/0669; A61B 1/00172
See application file for complete search history.

(56) References Cited

U.S. PATENT DOCUMENTS

2004/0151466 A1    8/2004  Crossman-Bosworth et al.
2004/0254474 A1   12/2004  Seibel et al.
(Continued)

FOREIGN PATENT DOCUMENTS

EP    2 742 848 A1     6/2014
JP    2008-504557 A    2/2008
(Continued)

OTHER PUBLICATIONS

Japanese Office Action dated Oct. 24, 2017 received in 2013-218227.
(Continued)

*Primary Examiner* — Tony Ko
(74) *Attorney, Agent, or Firm* — Scully, Scott, Murphy & Presser, P.C.

(57) ABSTRACT

A scanner includes: an optical fiber that guides light from a light source; a drive unit including at least one actuator that, when a voltage is applied thereto, displaces an exit end of the optical fiber in a direction intersecting an optical axis; a support portion that is provided on a basal end side from the drive unit and that is spaced away from the drive unit to support the optical fiber; and a correction portion that performs correction so as to bring the center of gravity of the drive unit and a combined center of gravity of the optical fiber, the drive unit, and the support portion close to each other on a cross-section of the drive unit.

5 Claims, 9 Drawing Sheets

(51) Int. Cl.
  *G02B 23/24*    (2006.01)
  *A61B 1/00*    (2006.01)
  *A61B 1/07*    (2006.01)

(52) U.S. Cl.
  CPC ............ *A61B 1/07* (2013.01); *G02B 23/2484* (2013.01); *G02B 23/26* (2013.01)

(56) References Cited

U.S. PATENT DOCUMENTS

| | | |
|---|---|---|
| 2005/0173817 A1 | 8/2005 | Fauver et al. |
| 2007/0242330 A1 | 10/2007 | Rosman et al. |
| 2010/0177368 A1* | 7/2010 | Kobayashi ............ A61B 1/0008 359/198.1 |
| 2014/0031679 A1 | 1/2014 | Tashiro et al. |
| 2014/0194692 A1 | 7/2014 | Yoshino et al. |

FOREIGN PATENT DOCUMENTS

| | | |
|---|---|---|
| JP | 2008-514970 A | 5/2008 |
| JP | 2010-162089 A | 7/2010 |
| JP | 2012-229976 A | 11/2012 |
| JP | 2014-121644 A | 7/2014 |
| JP | 2016-027880 A | 2/2016 |
| WO | 2004/068218 A2 | 8/2004 |
| WO | 2013/069382 A1 | 5/2013 |

OTHER PUBLICATIONS

Extended Supplementary European Search Report dated Apr. 21, 2017 in European Patent Application No. 14 85 5352.2.
International Search Report dated Dec. 16, 2014 issued in PCT/JP2014/075733.

* cited by examiner

SCANNER, SCANNING ILLUMINATOR, AND SCANNING OBSERVATION APPARATUS

CROSS-REFERENCE TO RELATED APPLICATIONS

This is a continuation of International Application PCT/JP2014/075733, with an international filing date of Sep. 26, 2014, which is hereby incorporated by reference herein in its entirety.

This application is based on Japanese Patent Application No. 2013-218227, filed on Oct. 21, 2013, the contents of which are incorporated herein by reference.

TECHNICAL FIELD

The present invention relates to scanners, scanning illuminators, and scanning observation apparatuses.

BACKGROUND ART

There is a known fiber-optic scanner that has a light-guiding cantilever optical fiber inside a tubular PZT (lead zirconate titanate) actuator and that supplies electrical power to pairs of electrodes provided on a surface of the PZT actuator to scan, in a desired pattern, the light emitted from a distal end of the cantilever optical fiber (refer to, for example, Patent Literature PTL 1 below). When a voltage is applied to the two pairs of electrodes, which are disposed in different quadrants on a cross-section of the PZT actuator such that the electrodes have phases shifted by 90° relative to one another, this fiber-optic scanner drives the cantilever optical fiber in two directions, thereby scanning light in a helical shape.

CITATION LIST

Patent Literature

{PTL 1}
PCT Japanese Translation Patent Publication No. 2008-504557

SUMMARY OF INVENTION

Technical Problem

The present invention provides a scanner, scanning illuminator, and scanning observation apparatus that allow a desired scanning trajectory to be achieved with high accuracy.

Solution to Problem

A first aspect of the present invention is a scanner including: an optical fiber that guides light from a light source; a drive unit including at least one actuator that, when a voltage is applied thereto, displaces an exit end of the optical fiber in a direction intersecting an optical axis; a support portion that is provided on a basal end side from the drive unit and that is spaced from the drive unit to support the optical fiber; and a correction portion that performs correction so as to bring the center of gravity of the drive unit and a combined center of gravity of the optical fiber, the drive unit, and the support portion close to each other on a cross-section of the drive unit.

A second aspect of the present invention is a scanning illuminator including: a light source that generates light to be guided to the aforementioned optical fiber; any of the aforementioned scanners; and a light-focusing lens that focuses illumination light scanned by the scanner onto an irradiated subject.

A third aspect of the present invention is a scanning observation apparatus including: the aforementioned scanning illuminator; and a light detection unit that receives return light of light radiated from the scanning illuminator onto an irradiated subject and detects the intensity of the return light.

DESCRIPTION OF EMBODIMENTS

A scanner, a scanning illuminator, and a scanning observation apparatus according to a first embodiment of the present invention will now be described with reference to the drawings.

Figure 1:
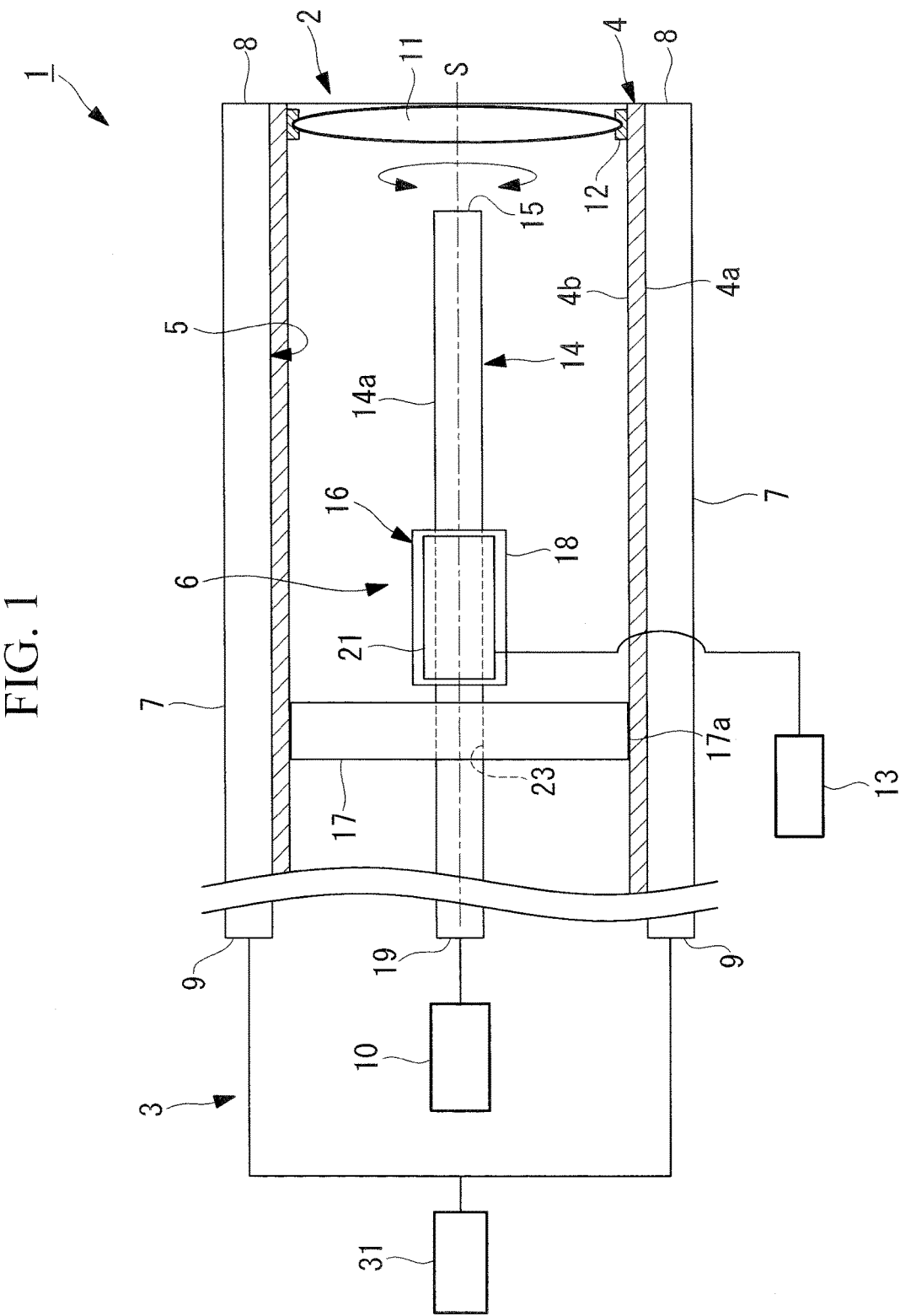
FIG. 1 is a diagram depicting a scanning observation apparatus according to a first embodiment of the present invention.

As shown in FIG. 1, a scanning observation apparatus 1 according to this embodiment includes: a cylindrical apparatus main body 4; a scanning illuminator 2 that is accommodated inside the apparatus main body 4 and irradiates a surface of an irradiated subject P with illumination light; and a light detection unit 3 that receives return light (e.g., reflected light, fluorescence) from the irradiated subject P, namely, return light of the illumination light radiated from the scanning illuminator 2 onto the surface of the irradiated subject P, and that detects the intensity of the return light.

As shown in FIG. 1, the scanning illuminator 2 includes: a light source 10 that generates illumination light; a scanner 6 according to this embodiment that one-dimensionally scans the illumination light emitted from the light source 10; a light-focusing lens 11 that focuses the illumination light; and a control unit 13 that controls the scanner 6.

Figure 2:
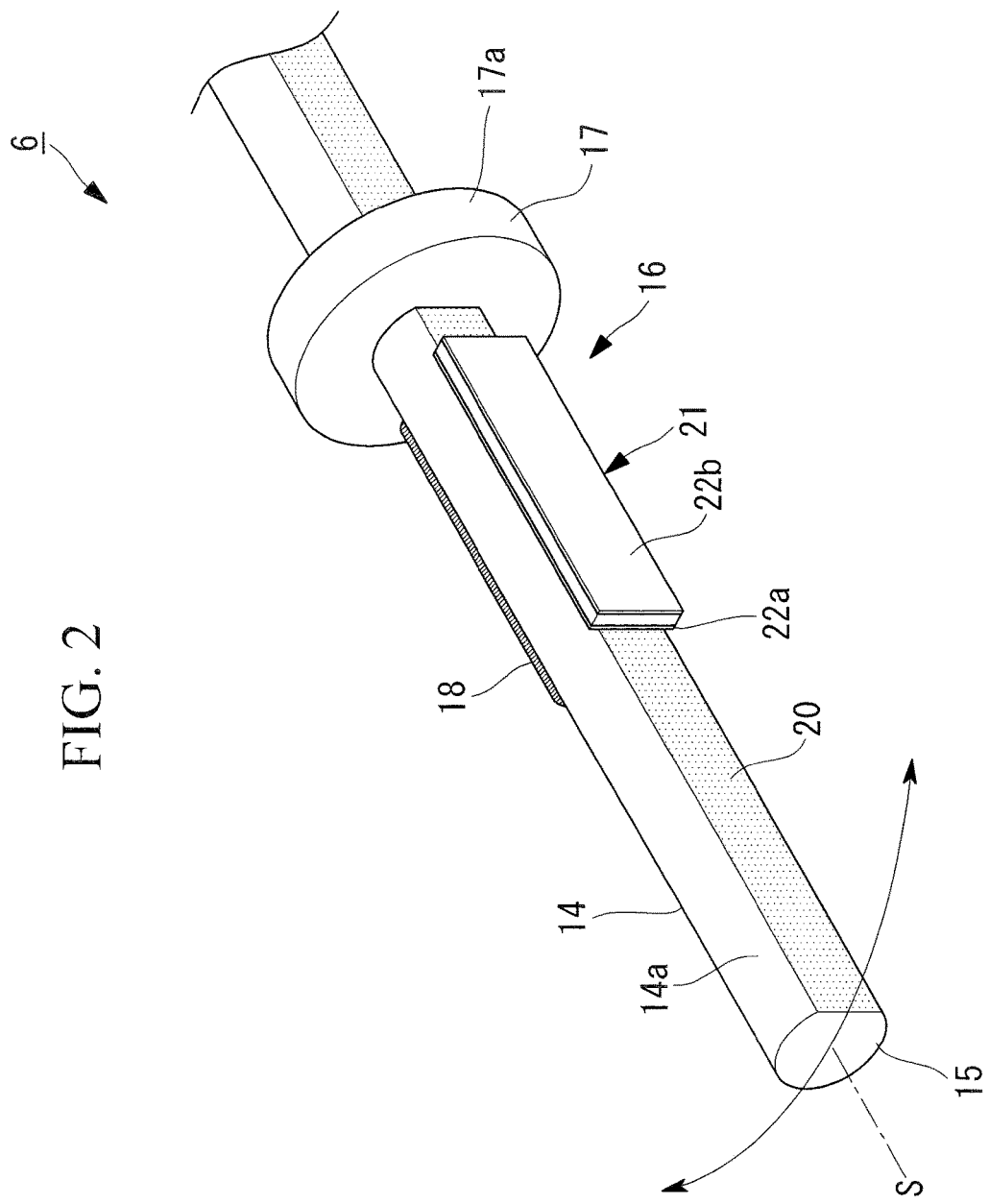
FIG. 2 is a perspective view of a scanner according to the first embodiment of the present invention provided in the scanning illuminator of FIG. 1.
Figure 4:
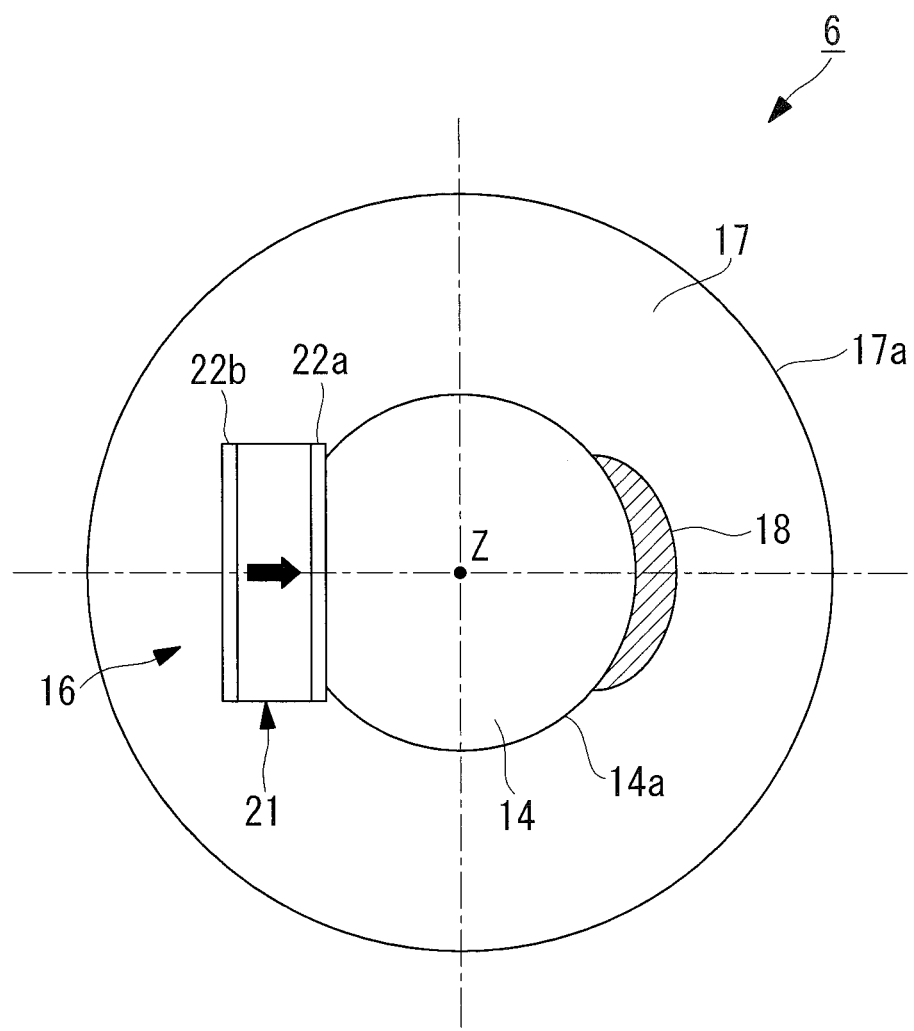
FIG. 4 is a cross-section of the drive unit, as viewed from the exit end of the optical fiber, after the correction portion of the scanner according to the first embodiment of the present invention has been provided.

As shown in FIGS. 2 and 4, the scanner 6 according to this embodiment includes: an optical fiber 14 that guides the illumination light emitted from the light source 10; a drive unit 16 that scans the illumination light emitted from an exit end 15 of the optical fiber 14; a support portion 17 that supports the optical fiber 14; and a correction portion 18 that corrects the center of gravity of the drive unit 16.

As shown in FIG. 2, the optical fiber 14 has a flat surface section 20 composed of a flat surface substantially parallel to an optical axis S such that the flat surface section 20 is formed in a part of an outer surface 14a in the circumferential direction.

As shown in FIGS. 2 and 4, the drive unit 16 includes: a single actuator 21 fixed to the flat surface section 20; the optical fiber 14 serving as a section to which the actuator 21 is fixed; and a correction portion 18.

The actuator 21 is electromagnetic or piezoelectric and includes electrodes 22a and 22b on both surfaces in the thickness direction. When a drive voltage is applied to the electrodes 22a and 22b, the actuator 21 produces an oscillation with a direction and an amplitude based on the applied voltage signal. Because the actuator 21 is fixed to the optical fiber 14 with the electrode 22a in contact with the flat surface section 20, the actuator 21 can propagate its oscillation to the optical fiber 14 so as to oscillate the exit end 15 of the optical fiber 14 in one axial direction orthogonal to the flat surface section 20.

As shown in FIGS. 1 and 2, the support portion 17 is a ring-shaped member that is provided away from the drive unit 16 towards the longitudinal basal end of the apparatus main body 4 and that includes a through-hole 23 in the thickness direction thereof along the longitudinal axis of the apparatus main body 4. The optical fiber 14 is fixed in the support portion 17 so as to penetrate the through-hole 23, and an outer surface 17a of the support portion 17 is in close contact with an inner surface 4b of the apparatus main body 4.

Furthermore, the support portion 17 fixes the optical fiber 14 to the apparatus main body 4 at a position towards the basal end from the drive unit 16 so that the oscillation propagated from the drive unit 16 to the optical fiber 14 can be inhibited from being propagated towards the basal end beyond the support portion 17.

Figure 3:
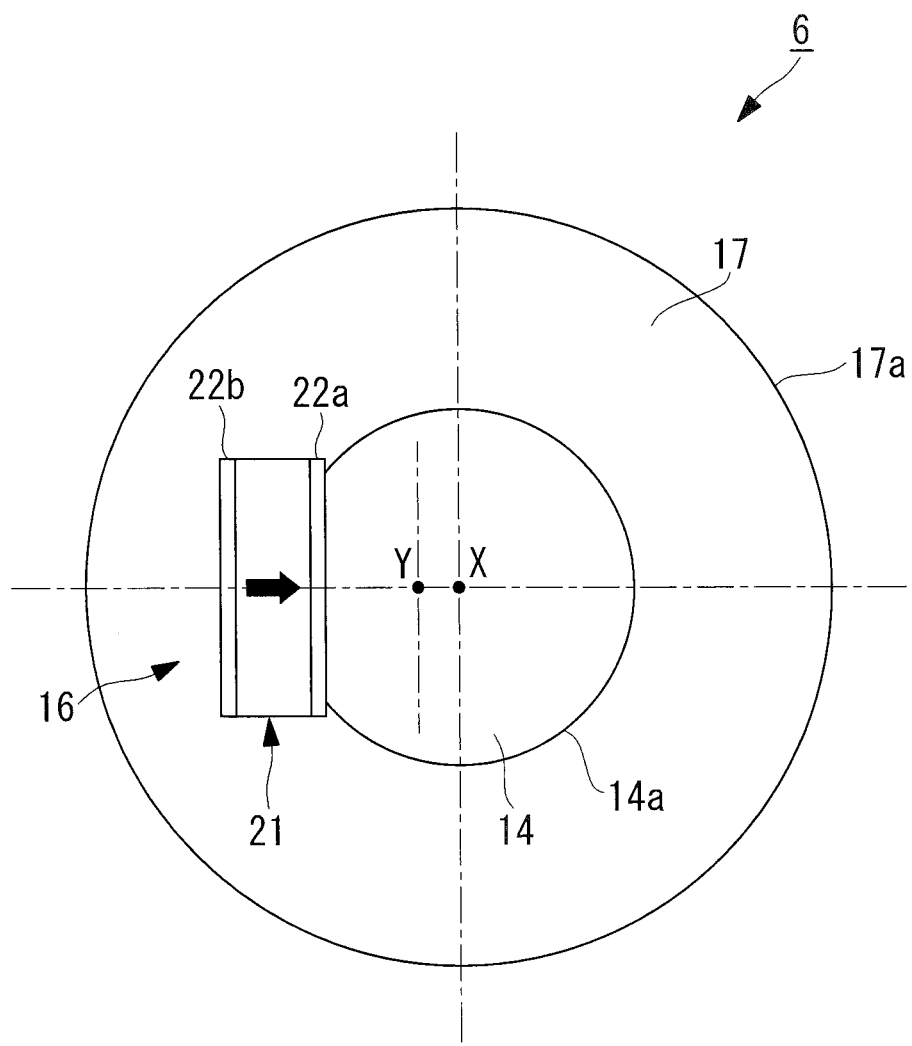
FIG. 3 is a cross-section of a drive unit, as viewed from the exit end of an optical fiber, before a correction portion of the scanner according to the first embodiment of the present invention is provided.

As shown in FIGS. 2 and 4, the correction portion 18 is an adhesive. The correction portion 18 is fixed to part of the optical fiber 14 and adjusts a center of gravity Y of the scanner 6 on a cross-section of the drive unit 16 to a center of gravity Z, shown in FIG. 4, at which the two centers of gravity X and Y shown in FIG. 3 coincide with each other.

As shown in FIG. 1, the light-focusing lens 11 is held at a lens support portion 12, which is provided on the inner surface 4b of the apparatus main body 4 and closer to the distal end side than the scanner 6 is, and converges illumination light scanned by the scanner 6 onto the surface of the irradiated subject P.

As shown in FIG. 1, the control unit 13 supplies a voltage signal based on a predetermined scanning trajectory to the actuator 21 such that the illumination light emitted from the exit end 15 of the optical fiber 14 forms a predetermined scanning trajectory input by the user.

As shown in FIG. 1, the light detection unit 3 includes detecting optical fibers 7 that receive return light from the irradiated subject P and guide it to the basal end side of the apparatus main body 4 and a sensor 31 that detects the intensity of the return light guided by the detecting optical fibers 7.

As shown in FIG. 1, the plurality of detecting optical fibers 7 extend along a longitudinal direction and are arranged in a circumferential direction on the outer circumferential surface 4a of the apparatus main body 4, with the light-entrance ends 8 oriented towards the front.

The sensor 31 receives the return light guided by these detecting optical fibers 7 simultaneously to detect the total intensity of the return light.

The operation of the scanning observation apparatus 1 with the above-described structure according to this embodiment will now be described.

When a voltage signal is supplied from the control unit 13 to the electrodes 22a and 22b of the actuator 21, the actuator 21 is oscillated in a manner corresponding to the supplied voltage signal, and that oscillation is propagated from the actuator 21 to the optical fiber 14. When the oscillation is propagated to the optical fiber 14, the exit end 15 of the optical fiber 14 is greatly oscillated in one axial direction due to resonance. When the illumination light that has been guided through the optical fiber 14 is emitted from the exit end 15 in a state where the exit end 15 is greatly oscillated in one axial direction, the illumination light can be oscillated in a direction intersecting the optical axis S of the optical fiber 14 so as to scan the surface of the irradiated subject P.

In other words, according to the scanning observation apparatus 1 of this embodiment, illumination light that has been emitted from the light source 10 of the scanning illuminator 2 and has exited from the exit end 15 of the optical fiber 14 is scanned by the scanner 6 in a direction intersecting the optical axis S, is focused by the light-focusing lens 11, and is radiated onto the surface of the irradiated subject P as a spot of light.

Thereafter, the return light from the irradiated subject P as a result of being irradiated with the illumination light is incident upon the light-entrance ends 8 of the detecting optical fibers 7 and is received by the sensor 31 through the detecting optical fibers 7. By doing so, each of the scanning positions of the optical fiber 14 scanned by the scanner 6 is associated with the intensity of return light received by the sensor 31, thereby allowing an image of a strain-free return light distribution to be generated.

In this case, because the center of gravity Y of the scanner 6 is corrected by the correction portion 18 provided on the drive unit 16 so as to coincide with the center of gravity X of the drive unit 16, as shown in FIG. 4, an advantage is afforded in that a desired scanning trajectory faithfully reflecting the applied voltage signal can be achieved with high accuracy in the form of a scanning trajectory of the exit end 15 of the optical fiber 14.

According to the scanner 6 of this embodiment, because the actuator 21 is fixed to the flat surface section 20 of the optical fiber 14, the actuator 21 and the outer surface 14a of the optical fiber 14 are in stable contact with each other via a large region of the contacting surface. By doing so, displacement of the actuator 21 and the optical fiber 14 relative to each other when oscillation is propagated from the actuator 21 to the optical fiber 14 is controlled, and propagation of the oscillation in a desired direction can be efficiently performed.

This embodiment has been described by way of example of the optical fiber 14 including the flat surface section 20 but is not limited to this as long as the optical fiber guides the illumination light.

This embodiment has been described by way of example of the correction portion 18 as an adhesive but is not limited to this. Any member, such as resin or metal member, may be fixed with an adhesive.

For the correction portion 18, not only members that completely match the two centers of gravity X and Y, but also members that bring the two centers of gravity X and Y close to each other are also acceptable.

A scanner 24, a scanning illuminator 25 (not shown in the drawings), and a scanning observation apparatus 26 (not shown in the drawings) according to a second embodiment of the present invention will now be described with reference to the drawings.

In describing this embodiment, components with the same structures as those of components used in the scanner 6, the scanning illuminator 2, and the scanning observation apparatus 1 according to the first embodiment are denoted by the same reference signs, and thus will not be described.

Figure 5:
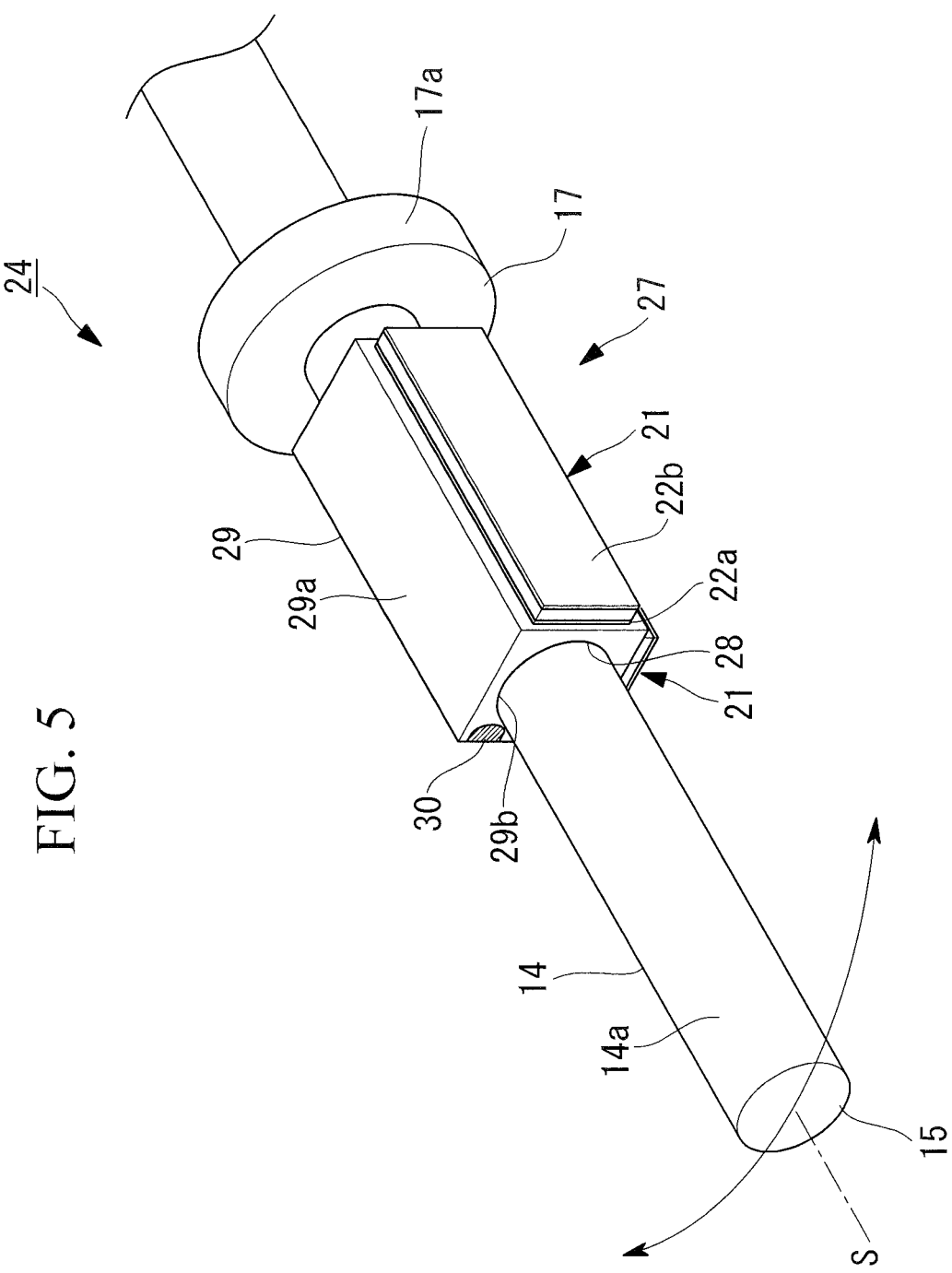
FIG. 5 is a perspective view of a scanner according to a second embodiment of the present invention.
Figure 7:
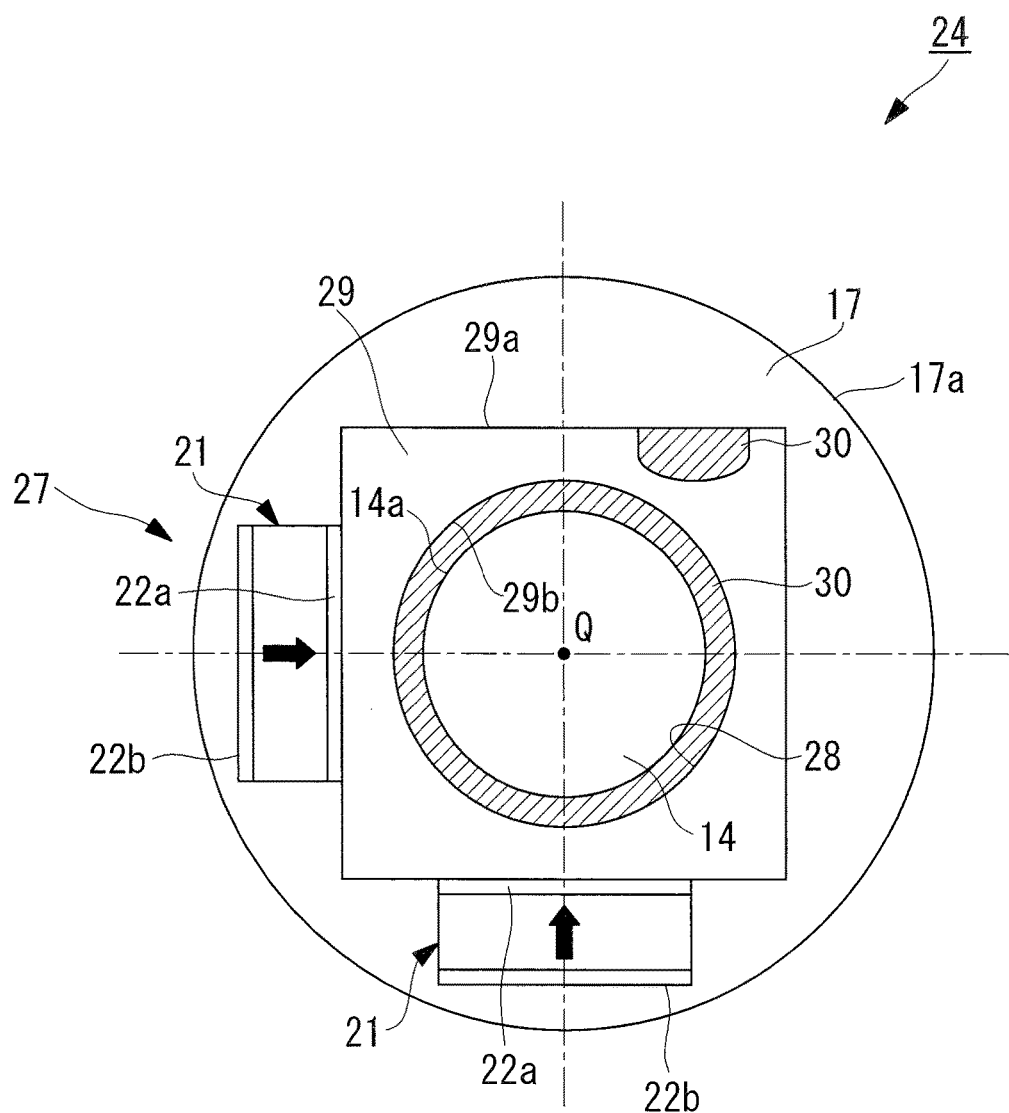
FIG. 7 is a cross-section of the drive unit, as viewed from the exit end of the optical fiber, after the correction portion of the scanner according to the second embodiment of the present invention has been provided.

As shown in FIGS. 5 and 7, in the scanner 24 according to this embodiment, a drive unit 27 includes a rectangular tubular oscillation propagation member 29 having an axial through-hole 28 through which the optical fiber 14 passes. The scanner 24 differs from the scanner 6 according to the first embodiment in that the actuators 21 are fixed to two respective outer surfaces 29a adjacent to each other in the circumferential direction of the oscillation propagation member 29.

The actuators 21 fixed to the neighboring outer surfaces 29a of the rectangular tubular oscillation propagation member 29 are arranged with their oscillation directions being shifted by substantially 90°.

Figure 6:
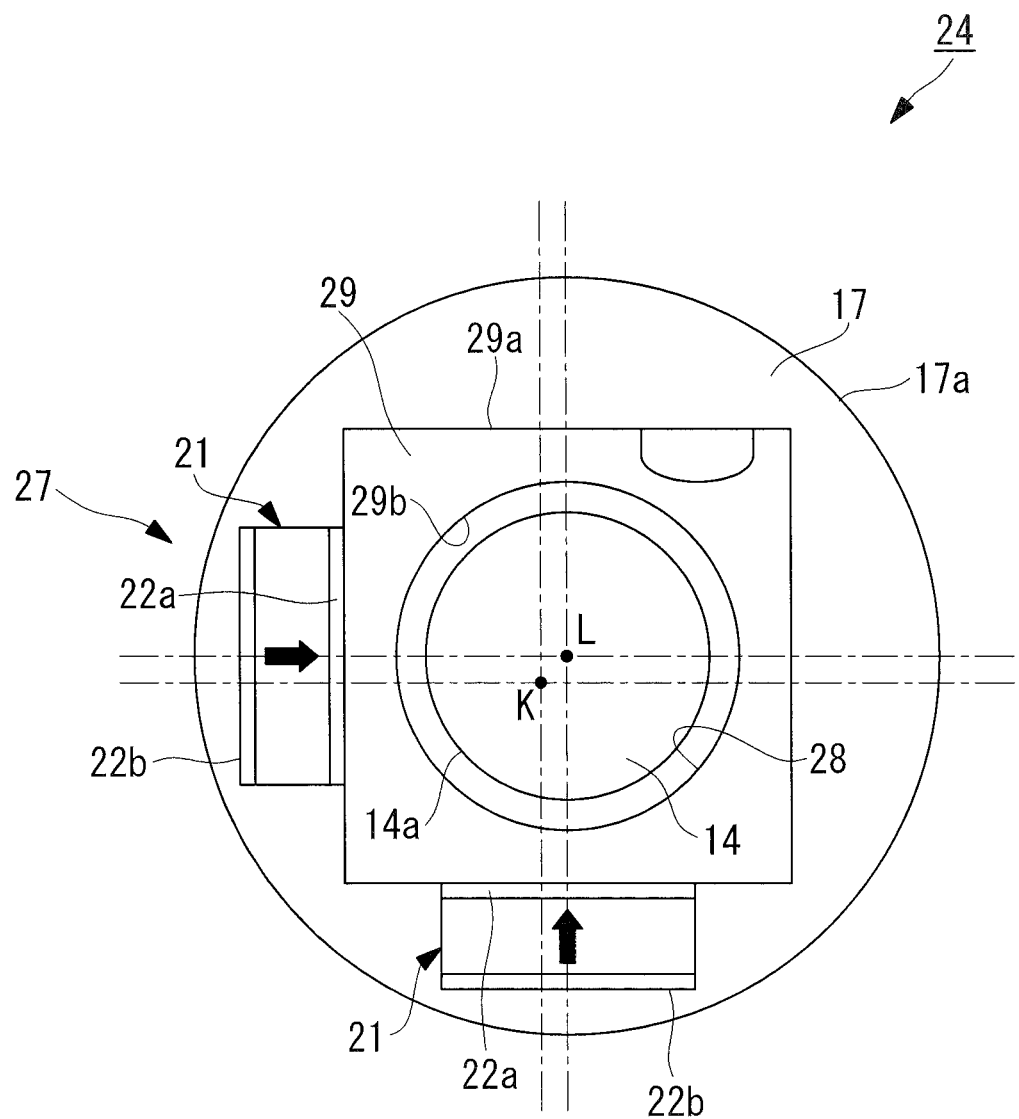
FIG. 6 is a cross-section of a drive unit, as viewed from the exit end of an optical fiber, before a correction portion of the scanner according to the second embodiment of the present invention is provided.

As shown in FIG. 7, a correction portion 30 is made of an adhesive fixed to an outer surface 29a and/or an inner surface 29b of the oscillation propagation member 29. The correction portion 30 adjusts the center of gravity K of the scanner 24 and the center of gravity L of the drive unit 27 shown in FIG. 6, on a cross-section of the drive unit 27, so that the two centers of gravity K and L are corrected to be the center of gravity Q, where the positions K and L coincide with each other.

The operation of the scanner 24, the scanning illuminator 25 (not shown in the figure), and the scanning observation apparatus 26 (not shown in the figure) according to this embodiment with the above-described structure will now be described.

When a voltage signal is supplied to each of the electrodes 22a and 22b of the two actuators 21 from the control unit 13, the exit end 15 of the optical fiber 14 can be displaced in two axial directions substantially orthogonal to each other.

Then, by adjusting the amplitude and phase of the voltage signal supplied to each of the electrodes 22a and 22b of the actuators 21, the exit end 15 of the optical fiber 14 can be displaced two-dimensionally along an arbitrary trajectory. By doing so, the illumination light emitted from the exit end 15 of the optical fiber 14 can be scanned two-dimensionally.

For example, by supplying the two actuators 21 with voltage signals that are sine waves having linearly decreasing amplitudes and phases shifted by 90° relative to each other, illumination light in a helical shape can be radiated onto the surface of the irradiated subject P.

In this case, according to the scanner 24 of this embodiment, because the center of gravity L of the drive unit 27 is adjusted by the correction portion 30, illumination light can be radiated onto a position corresponding to the voltage signal with high accuracy. As a result, an advantage is afforded in that the scanning position of the illumination light corresponding to the voltage signal can be made to highly accurately coincide with an actual radiation position of the illumination light, thereby making it possible to generate a strain-free return light image on the basis of information about the scanning position and the intensity of return light detected by the sensor 31.

Also in this embodiment, because each of the actuators 21 is stably fixed to the outer surfaces 29a on a flat surface of the oscillation propagation member 29, displacement of the actuators 21 relative to the oscillation propagation member 29 can be controlled, thereby efficiently oscillating the optical fiber 14 held in the through-hole 28.

Figure 8:
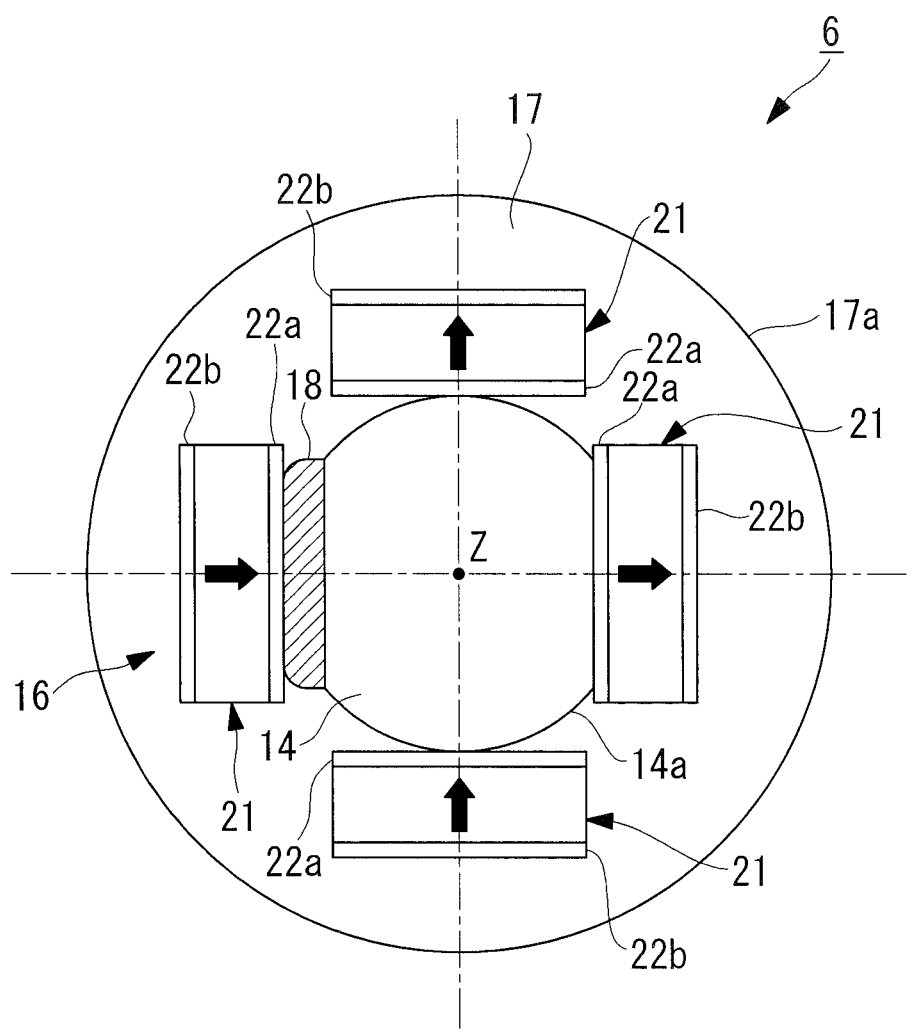
FIG. 8 is a cross-section of a drive unit of a scanner according to a modification of the first embodiment of the present invention, as viewed from the exit end of an optical fiber.
Figure 9:
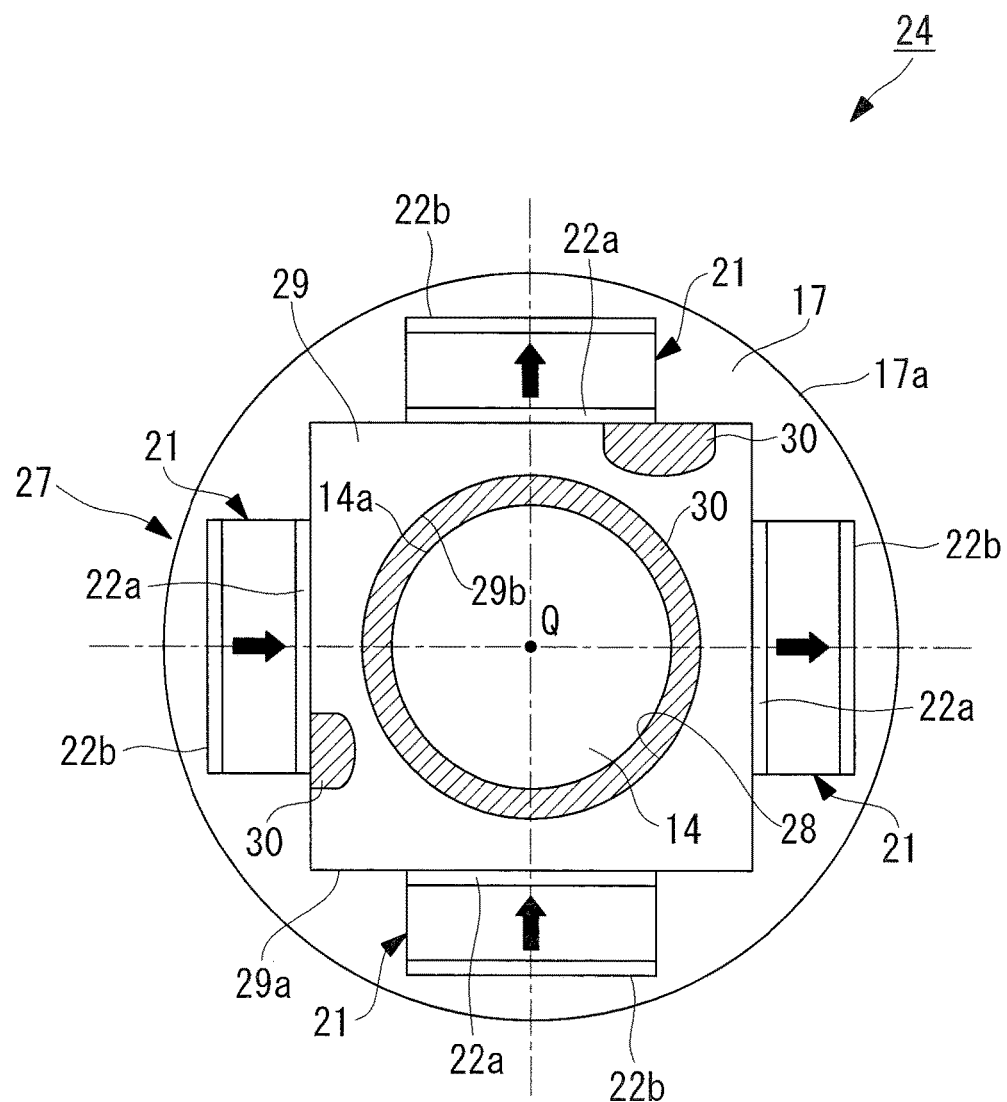
FIG. 9 is a cross-section of a drive unit of a scanner according to a modification of the second embodiment of the present invention, as viewed from the exit end of an optical fiber.

As shown in FIGS. 8 and 9, in the scanners 6 and 24 according to the above-described embodiments, the drive units 16 and 7 may include four actuators 21 that provide oscillation in the radial direction of the optical fiber 14, so that the actuators 21 may be disposed adjacent to one another and spaced apart from one another at substantially 90° intervals in the circumferential direction of the optical fiber 14. In addition, three actuators 21 or five or more actuators 21 may be provided.

As described above, according to this embodiment, when a voltage is applied to the actuator in a state where the optical fiber is supported at the support portion, the electrical energy is converted into kinetic energy for oscillating the optical fiber, and oscillation with a direction and an amplitude based on the applied voltage signal is propagated from the actuator to the optical fiber. Thereafter, as the oscillation propagated to the optical fiber advances away from the support portion and approaches the exit end of the optical fiber, the amplitude of the oscillation becomes larger due to resonance, thereby allowing the drive unit to scan the light emitted from the exit end of the optical fiber in a direction intersecting the optical axis.

In this case, the correction portion performs correction such that the center of gravity of the scanner, namely, the combined center of gravity of the optical fiber, the drive unit, and the support portion arranged away from the drive unit, and the center of gravity of the drive unit are brought closer to each other on a cross-section of the drive unit. For this reason, even if the center of gravity of the drive unit does not coincide with the center of gravity of the scanner, the two centers of gravity can be corrected using the correction portion, thereby allowing a desired scanning trajectory as specified by the applied voltage signal to be achieved with high accuracy in the form of the scanning trajectory of the exit end of the optical fiber.

As described above, the drive unit may be fixed to a flat surface section that is formed in a part of an outer surface of at least the optical fiber and that is substantially parallel to the optical axis.

By doing so, the extent of the contacting surface between the drive unit and the outer surface of the optical fiber can be enlarged. As a result, relative displacement between the drive unit and the optical fiber when oscillation is propagated from the drive unit to the optical fiber can be controlled, thereby efficiently propagating oscillation in a desired direction.

As described above, the drive unit may include a polygonal tubular oscillation propagation member that has a through-hole in an axial direction thereof and that is composed of a material capable of propagating oscillation, the optical fiber may pass through the through-hole of the oscillation propagation member, and the actuator may be fixed to the outer surface of the oscillation propagation member.

By doing so, the extent of the contacting surface between the actuator and the oscillation propagation member can be enlarged on a cross-section of the drive unit. As a result, relative displacement between the actuator and the oscillation propagation member when oscillation is propagated from the actuator to the oscillation propagation member can be controlled, thereby efficiently propagating oscillation to the optical fiber held in the through-hole.

As described above, the actuator may displace the exit end of the optical fiber in one axial direction.

By doing so, when a voltage is applied, the actuator can displace the exit end of the optical fiber one-dimensionally, thereby allowing light emitted from the exit end of the optical fiber to be scanned one-dimensionally.

As described above, the drive unit may include at least two of the actuators, which produce oscillations in a radial direction of the optical fiber, and the actuators adjacent to each other in a circumferential direction may be arranged so as to be spaced apart by substantially 90° in a circumferential direction of the optical fiber.

By doing so, the exit end of the optical fiber can be displaced in two axial directions substantially orthogonal to each other. As a result of the center of gravity being corrected, the exit end of the optical fiber can be placed at a position corresponding to the applied voltage with high accuracy, thereby allowing illumination light to be radiated according to a desired scanning trajectory. When, for example, voltages with phases shifted by 90° and linearly changing amplitudes are applied to the actuators adjacent to each other in the circumferential direction, the exit end of the optical fiber can be displaced in a helical shape with high accuracy, thereby allowing illumination light emitted from the exit end of the optical fiber to be scanned two-dimensionally in a helical shape.

According to the above-described scanning illuminator, because the diffusing illumination light emitted from the exit end of the optical fiber is focused by the light-focusing lens, the illumination light is radiated onto the irradiated subject as a spot of light.

According to the above-described scanning observation apparatus, when each of the irradiation positions at which light is radiated onto the irradiated subject by the scanning illuminator in precise accordance with a desired trajectory is associated with the intensity of return light from each of the irradiation positions, a strain-free return light distribution can be acquired.

The present invention affords an advantage in that a desired scanning trajectory can be achieved with high accuracy.

REFERENCE SIGNS LIST

1 Scanning observation apparatus
2 Scanning illuminator
3 Light detection unit
6, 24 Scanner
10 Light source
11 Light-focusing lens
14 Optical fiber
14a Outer surface of optical fiber
15 Exit end of optical fiber
16, 27 Drive unit
17 Support portion
18, 30 Correction portion
20 Flat surface section
21 Actuator
28 Through-hole of oscillation propagation member
29 Oscillation propagation member

The invention claimed is:

1. A scanner comprising:
an optical fiber that guides light from a light source;
a drive unit comprising at least one actuator that, when a voltage is applied thereto, displaces an exit end of the optical-fiber in a direction intersecting an optical axis;
a support portion that is provided on a basal end side from the drive unit and that is spaced from the drive unit to support the optical fiber; and
a correction portion that is configured to shift a first combined center of gravity of both of the drive unit and the correction portion, so that the combined center of gravity substantially coincides with a second combined center of gravity of both of the optical fiber and the support portion in a radial cross section of the optical fiber,
wherein the drive unit comprises a polygonal tubular oscillation propagation member that has a through-hole in an axial direction thereof and that is composed of a material configured to propagate oscillation, wherein the optical fiber passes through the through-hole of the oscillation propagation member, and the actuator is fixed to the outer surface of the oscillation propagation member, and
wherein the drive unit comprises at least two of the actuators, which produces oscillations in a radial direction of the optical fiber, and the actuators adjacent to each other in a circumferential direction are arranged so as to be spaced apart by substantially 90° in a circumferential direction of the optical fiber.

2. The scanner according to claim 1,
wherein the drive unit is fixed to a flat surface section that is formed in a part of an outer surface of at least the optical fiber and that is substantially parallel to the optical axis.

3. The scanner according to claim 1,
wherein the actuator displaces the exit end of the optical fiber in one axial direction.

4. A scanning illuminator comprising:
a light source that generates light to be guided to the optical fiber;
the scanner according to claim 1; and
a light-focusing lens that focuses light scanned by the scanner onto an irradiated subject.

5. A scanning observation apparatus comprising:
the scanning illuminator according to claim 4; and
a light detection unit that receives return light of light radiated from the scanning illuminator onto an irradiated subject and detects the intensity of the return light.

* * * * *